United States Patent
Ordonez et al.

(10) Patent No.: US 10,172,716 B1
(45) Date of Patent: Jan. 8, 2019

(54) CORPECTOMY SPACER AND PLATE

(71) Applicant: Choice Spine, LP, Knoxville, TN (US)

(72) Inventors: Bernardo Jose Ordonez, Virginia Beach, VA (US); Benjamin G. Harder, Knoxville, TN (US); Stephen Ainsworth, Knoxville, TN (US)

(73) Assignee: Choice Spine, LLC, Knoxville, TX (US)

( * ) Notice: Subject to any disclaimer, the term of this patent is extended or adjusted under 35 U.S.C. 154(b) by 0 days.

(21) Appl. No.: 15/693,815

(22) Filed: Sep. 1, 2017

Related U.S. Application Data

(60) Provisional application No. 62/383,785, filed on Sep. 6, 2016.

(51) Int. Cl.
| | | |
|---|---|---|
| *A61F 2/44* | (2006.01) | |
| *A61B 17/70* | (2006.01) | |
| *A61B 17/86* | (2006.01) | |
| *A61F 2/30* | (2006.01) | |

(52) U.S. Cl.
CPC .............. *A61F 2/442* (2013.01); *A61F 2/447* (2013.01); *A61B 17/7059* (2013.01); *A61B 17/86* (2013.01); *A61F 2002/30841* (2013.01)

(58) Field of Classification Search
CPC ...... A61F 2/4455; A61F 2/4465; A61F 2/447; A61F 2002/4475; A61B 17/7059; A61B 17/80
See application file for complete search history.

(56) References Cited

U.S. PATENT DOCUMENTS

| | | | | |
|---|---|---|---|---|
| 6,342,055 B1* | 1/2002 | Eisermann | ............. | A61B 17/68 606/286 |
| 2004/0092929 A1* | 5/2004 | Zindrick | .................. | A61F 2/44 606/247 |
| 2014/0046447 A1* | 2/2014 | Dunworth | ............... | A61F 2/447 623/17.16 |
| 2015/0196398 A1* | 7/2015 | Camprasse | ............. | A61F 2/442 433/174 |

* cited by examiner

*Primary Examiner* — Julianna N Harvey
(74) *Attorney, Agent, or Firm* — Luedeka Neely Group, PC

(57) ABSTRACT

An intervertebral body spacer includes an inferior plate portion; a superior plate portion vertically spaced above the inferior plate portion; and a central spacer portion between the inferior plate portion. The central spacer portion has a posterior vertical wall extending between the inferior plate portion and the superior plate portion, the posterior vertical wall including multiple windows therethrough, an anterior vertical wall opposite and spaced apart from the posterior vertical wall, the anterior vertical wall being solid, and a pair of side vertical walls spaced apart from one another and extending between the posterior vertical wall and the anterior vertical wall, the side vertical walls including multiple windows.

3 Claims, 6 Drawing Sheets

CORPECTOMY SPACER AND PLATE

CROSS-REFERENCE TO RELATED APPLICATION

This application claims priority to U.S. Provisional Application No. 62/383,785 filed Sep. 6, 2016, entitled CORPECTOMY SPACER AND PLATE, incorporated herein by reference in its entirety.

FIELD

This disclosure relates to the field of corpectomy spacers. More particularly, this disclosure relates to a spacer configured to have plate portions to facilitate installation, and configured so that one or more of the plate portions can move in relation to a spacer portion.

BACKGROUND

Corpectomy spacers are implants used in surgical procedures to replace vertebrae or portions of vertebrae. Improvement is desired in the construction of corpectomy spacers used in spinal surgery.

The disclosure advantageously provides a spacer configured to facilitate installation, and configured to permit the spacer to be located for effectiveness.

SUMMARY

The disclosure relates to improved intervertebral body spacers.

In one aspect, an intervertebral body spacer includes an inferior plate portion; a superior plate portion vertically spaced above the inferior plate portion; and a central spacer portion between the inferior plate portion. The central spacer portion has a posterior vertical wall extending between the inferior plate portion and the superior plate portion. The posterior vertical wall includes multiple windows therethrough. A solid anterior vertical wall is located opposite and spaced apart from the posterior vertical wall. A pair of side vertical walls are spaced apart from one another and extend between the posterior vertical wall and the anterior vertical wall. The side vertical walls include multiple windows.

In another aspect, the intervertebral spacer includes a plate portion configured to receive a screw; and a central spacer portion connected to the plate portion. The central spacer portion has a posterior vertical wall including multiple windows therethrough. A solid anterior vertical wall is located opposite and spaced apart from the posterior vertical wall. A pair of side vertical walls are spaced apart from one another and extend between the posterior vertical wall and the anterior vertical wall. The side vertical walls include multiple windows.

In a further aspect, the intervertebral body spacer includes an inferior plate portion; a superior plate portion vertically spaced above the inferior plate portion; a central spacer portion between the inferior plate portion; and a weak point defined between the central spacer portion and either the inferior plate portion or the superior plate portion or both. The weak point is configured to fracture so the inferior plate portion or the superior plate portion or both can translate and move in relation to the central spacer portion.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
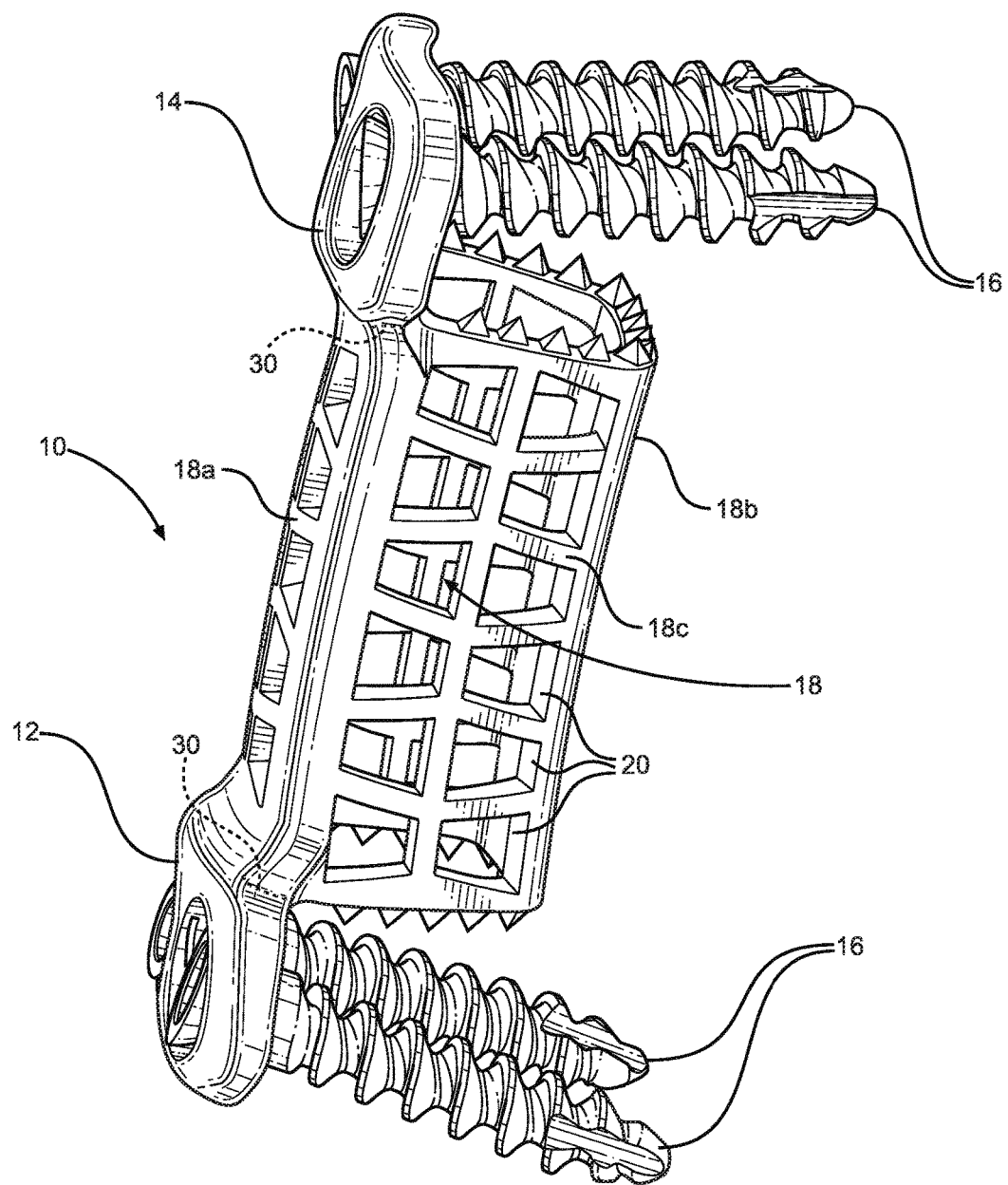
FIGS. 1 and 2 are perspective views of a corpectomy spacer and plate according to the disclosure, shown with screws for installation to the spine.
Figure 2:
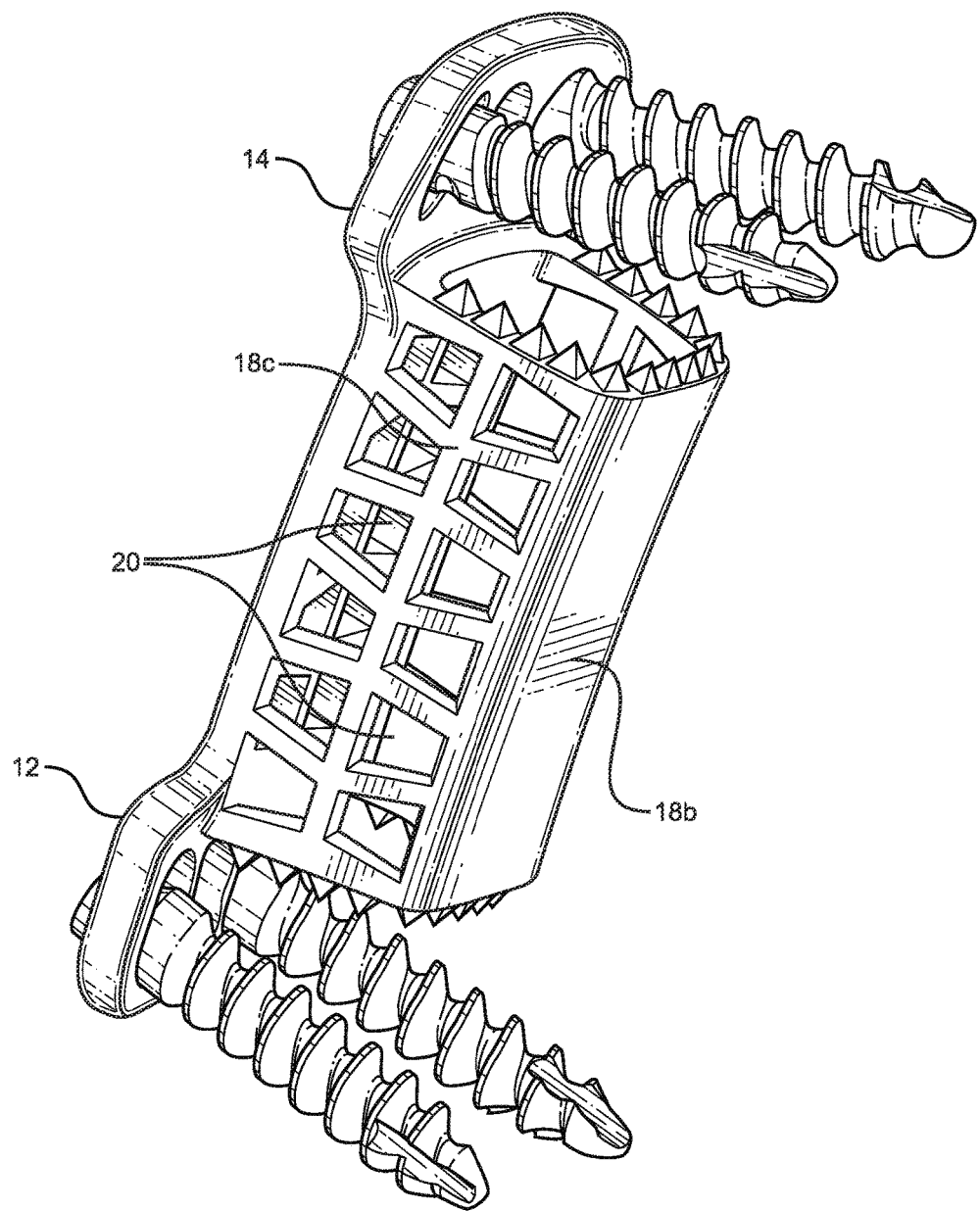
Figure 3:
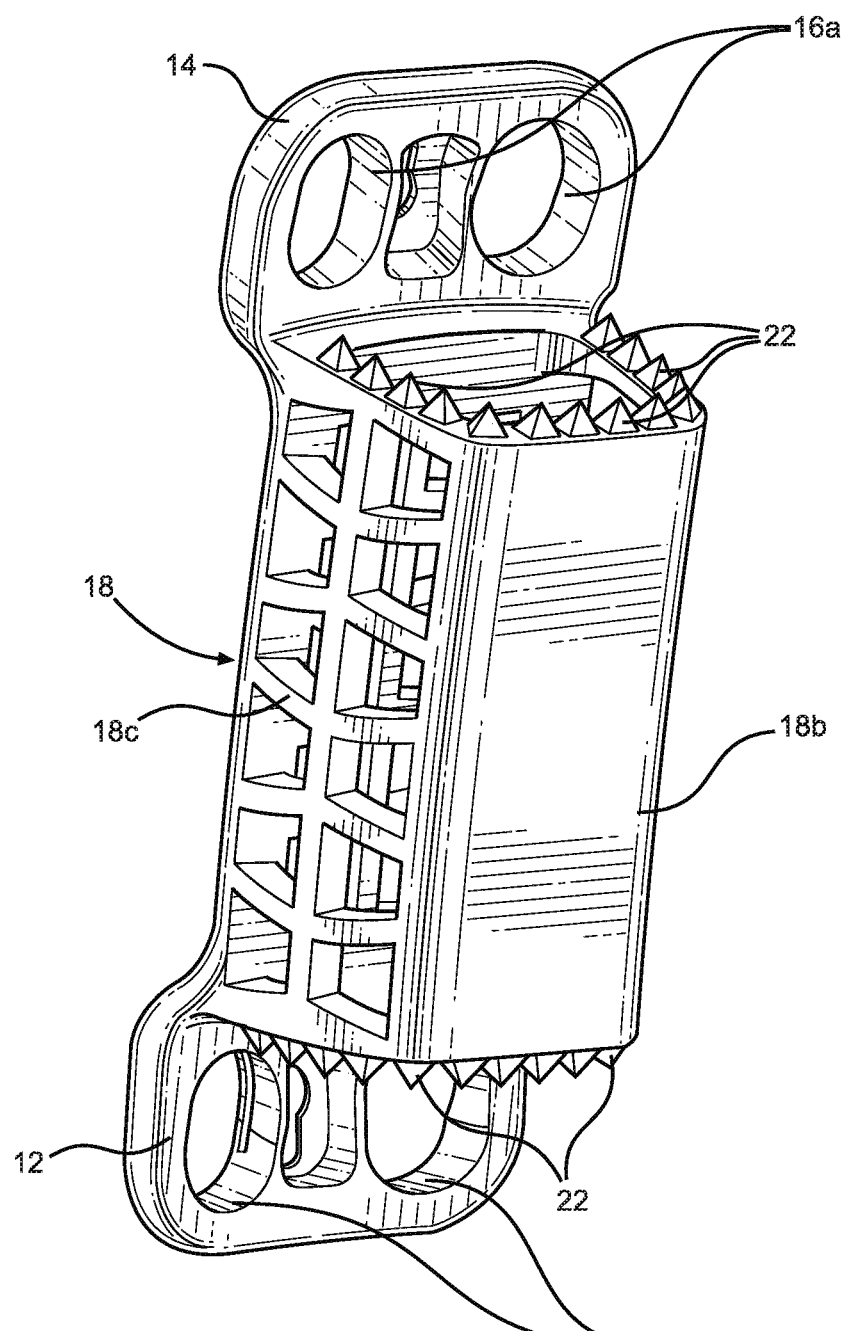
FIGS. 3-7 are further views of the corpectomy spacer and plate of FIGS. 1 and 2 from various vantages, without the screws.
Figure 4:
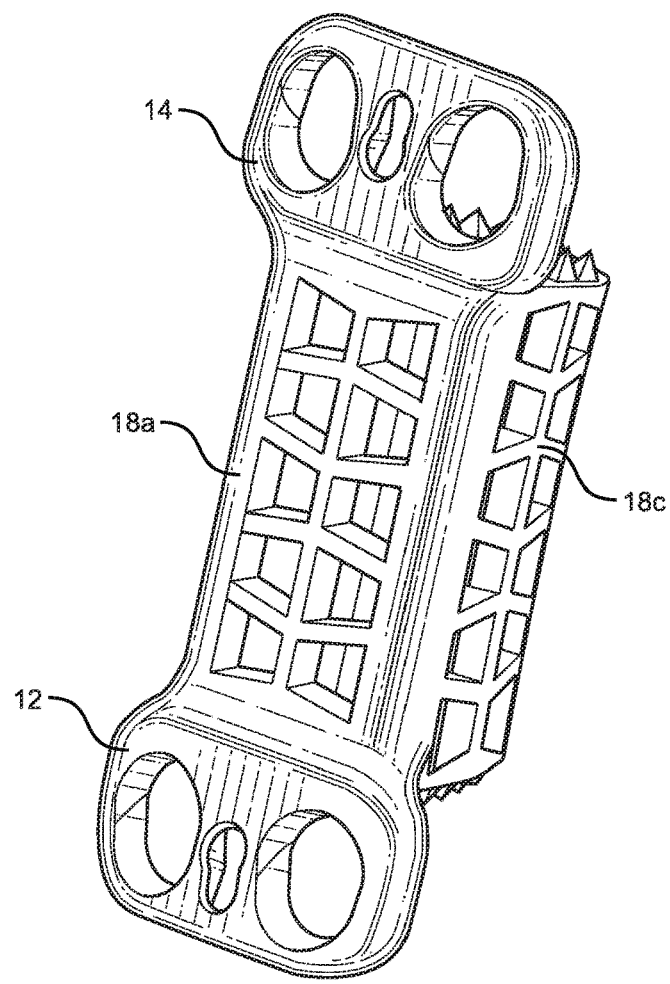
Figure 5:
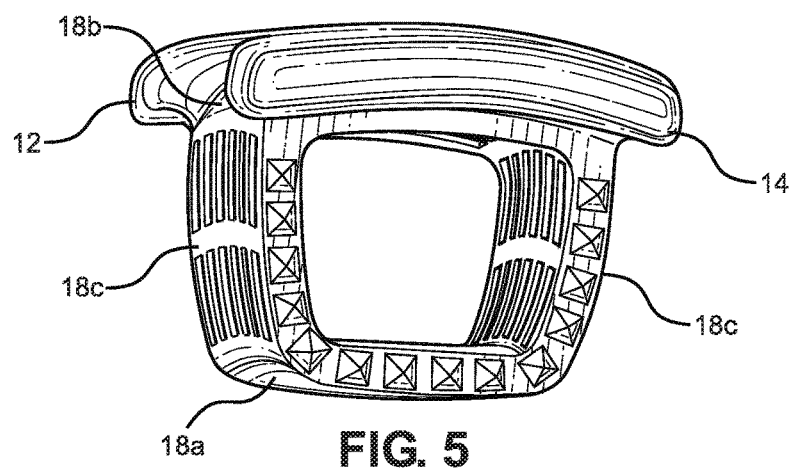

With reference to the drawings, there is shown an intervertebral body spacer 10 that has an inferior plate portion 12 and a superior plate portion 14 to allow screws 16 to be placed into adjacent vertebral bodies. A central spacer portion 18 is configured between the inferior plate portion 12 and the superior plate portion 14 to allow for maximum volume of bone graft to help achieve adjacent level bone fusion. In anatomical terminology, superior refers to what is above something, and inferior refers to what is below it. The spacer 10 is configured to be installed between adjacent vertebrae of the human spine, in which vertebra are vertically oriented relative to one another. The spacer 10 is also configured to have an aesthetically pleasing appearance.

The spacer portion 18 includes a posterior vertical wall 18a extending between the inferior plate portion 12 and the superior plate portion 14, an anterior vertical wall 18b opposite and spaced apart from the posterior vertical wall 18a, and a pair of side vertical walls 18c spaced apart from one another and extending between the posterior vertical wall and the anterior vertical wall. The walls 18a and 18c includes multiple windows 20 through the wall of the spacer portion 18 to help hold the bone graft and provide strength to the structure. The anterior vertical wall 18c is solid to prevent bone graft from entering the spinal cord area. Points 22 are desirably located at the upper and lower ends of the walls 18b and 18c to frictionally engage with the vertebrae.

The screws 16 are configured to retain the spacer portion 18 in place and prevent expulsion and provide additional fixation. Both sets of inferior and superior screw holes 16a allow for variation of screw placement angle. The superior or inferior screw holes, or both, may be a slotted design to allow for spacer settling and additional compression.

The spacer 10 may include a cone in the hole configured translate under the increasing compressive loads. Also, the spacer 10 may be configured to have a locking feature for preventing the installed screws from backing out. For example, the plate portions adjacent the screw holes 16a may include a slot containing a washer or clip, preferably made of nitinol that may be oval to match the screw hole. The screw passes past the washer or clip, which is then released to become positioned over the head of the screw to provide a physical locking barrier to prevent the screw from backing out once it has been placed.

Figure 6:
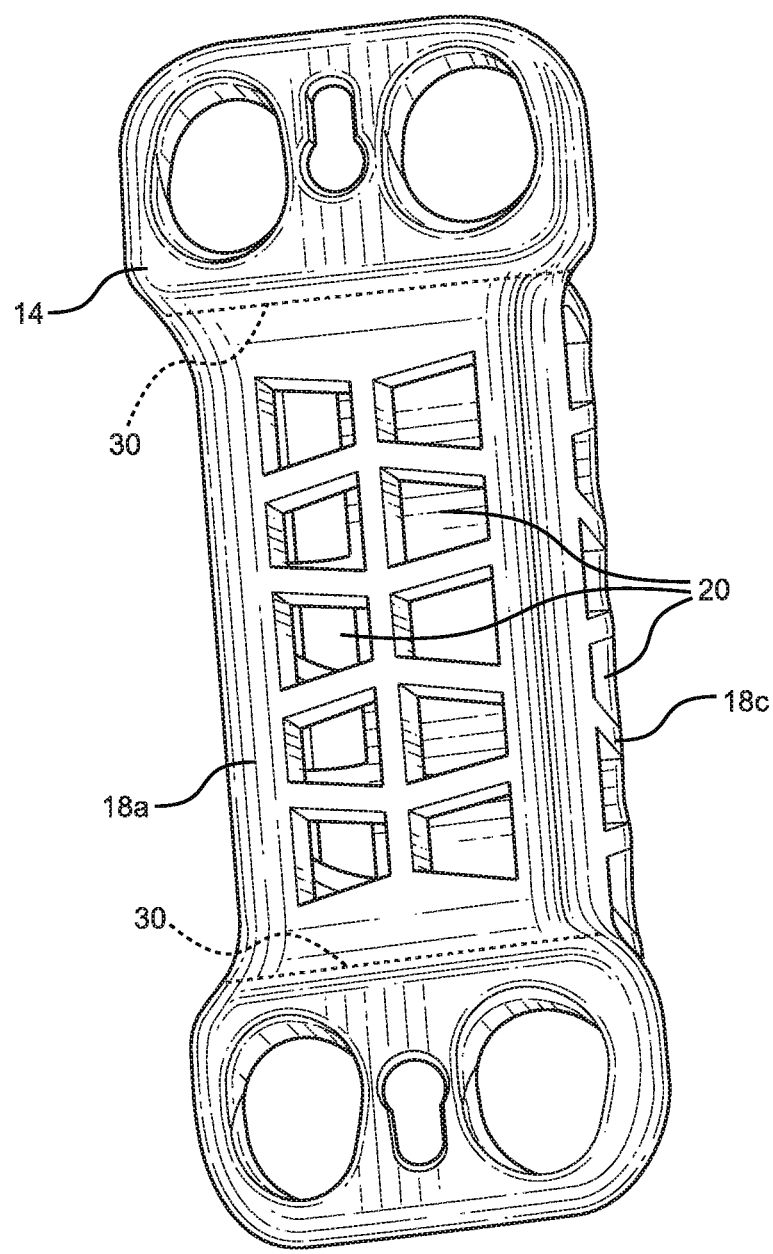
Figure 7:
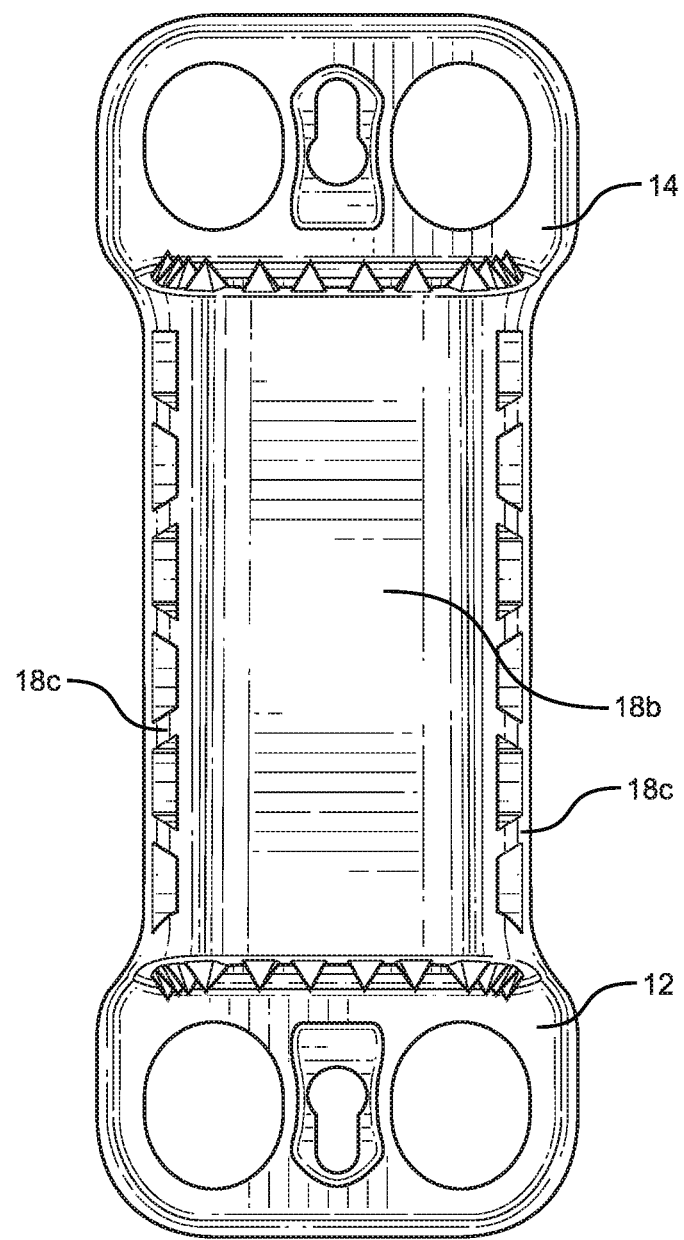

One or both of the plate portions 12/14 may be configured to move in relation to the central spacer portion 18. The spacer 10 may be made as a single piece, such as by 3-d printing, and then become 2-piece as compression increases and fractures along weak points, such as weak points 30 as depicted in FIGS. 1 and 6. The weak points 30 are configured to fracture so the plate portions 12/14 can translate and move in relation to the central spacer portion 18.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure.

The invention claimed is:

1. An intervertebral body spacer, comprising:
   an inferior plate portion;
   a superior plate portion vertically spaced above the inferior plate portion; and
   a central spacer portion having:
      a posterior vertical wall extending between the inferior plate portion and the superior plate portion, the posterior vertical wall including multiple windows therethrough,
      an anterior vertical wall opposite and spaced apart from the posterior vertical wall, the anterior vertical wall being solid,
      a pair of side vertical walls spaced apart from one another and extending between the posterior vertical wall and the anterior vertical wall, the side vertical walls including multiple windows; and
      a weak point defined between the central spacer portion and either the inferior plate portion or the superior plate portion or both, the weak point being configured to fracture as compressive loading on the intervertebral body spacer increases so the inferior plate portion or the superior plate portion or both can translate and move in relation to the central spacer portion when the intervertebral body spacer is implanted in a patient.

2. The intervertebral body spacer of claim 1, wherein the inferior plate portion is securable to an inferior vertebrae by inferior screws extending through inferior screw holes of the inferior plate portion and the superior plate portion is securable to a superior vertebrae by superior screws extending through superior screw holes of the superior plate portion, and wherein the inferior and the superior screw holes comprise slotted screw holes to enable the intervertebral body spacer to move after the inferior screws and the superior screws have been installed.

3. An intervertebral body spacer, comprising:
   an inferior plate portion;
   a superior plate portion vertically spaced above the inferior plate portion;
   a central spacer portion between the inferior plate portion and the superior plate portion; and
   a weak point defined between the central spacer portion and either the inferior plate portion or the superior plate portion or both, the weak point being configured to fracture as compressive loading on the intervertebral body spacer increases so the inferior plate portion or the superior plate portion or both can translate and move in relation to the central spacer portion when the intervertebral body spacer is implanted in a patient.

* * * * *